(12) United States Patent
Kavteladze et al.

(10) Patent No.: US 6,814,750 B2
(45) Date of Patent: Nov. 9, 2004

(54) IMPLANTABLE, SELF-EXPANDING PROSTHETIC DEVICE

(75) Inventors: Zaza A. Kavteladze, Moscow (RU); Aleksandr P. Korshok, Moscow (RU); Andrej A. Kadnikov, Moscow (RU); Palle Hansen, Roskilde (DK); Beth Ann Kirts, Bloomington, IN (US)

(73) Assignees: William Cook Europe A/S, Bjaeverskov (DK); Cook Incorporated, Bloomington, IN (US)

( * ) Notice: Subject to any disclaimer, the term of this patent is extended or adjusted under 35 U.S.C. 154(b) by 0 days.

(21) Appl. No.: 10/140,780

(22) Filed: May 7, 2002

(65) Prior Publication Data

US 2002/0128707 A1 Sep. 12, 2002

Related U.S. Application Data

(63) Continuation of application No. 09/645,179, filed on Aug. 24, 2000, now Pat. No. 6,383,216, which is a continuation of application No. 08/450,009, filed on May 25, 1995, now Pat. No. 6,336,938, which is a continuation-in-part of application No. 29/034,346, filed on Feb. 2, 1995, now Pat. No. Des. 380,831, which is a continuation-in-part of application No. 08/379,582, filed as application No. PCT/DK93/00256 on Aug. 6, 1993, now Pat. No. 5,643,339.

(30) Foreign Application Priority Data

Aug. 6, 1992 (RU) .............................. 5057852

(51) Int. Cl.[7] .................................. A61F 2/06
(52) U.S. Cl. ..................... 623/1.22; 623/1.15
(58) Field of Search .............................. 623/1.15, 1.17, 623/1.22; 606/194, 195

(56) References Cited

U.S. PATENT DOCUMENTS

| 4,503,569 A | 3/1985 | Dotter |
| 4,776,337 A | 10/1988 | Plamaz |
| 4,856,516 A | 8/1989 | Hillstead |
| 4,950,227 A | 8/1990 | Savin et al. |
| 5,116,365 A | 5/1992 | Hillstead |
| 5,133,732 A | 7/1992 | Wiktor |
| 5,135,536 A | 8/1992 | Hillstead |

(List continued on next page.)

FOREIGN PATENT DOCUMENTS

| DE | 3918736 | 12/1990 |
| EP | 0221570 | 5/1987 |
| EP | 423916 | * 4/1991 |
| EP | 0464755 | 1/1992 |
| EP | 0645125 | 3/1995 |
| SU | 1237201 | 6/1986 |

OTHER PUBLICATIONS

Brady, George S. et al.; *Materials Handbook*: Twelfth Edition; 1986; ppg. 300–301.

Rosch, J., et al.; "Modified Gianturco Expandable Wire Stents in Experimental and Clinical Use"; *Ann. Radiol.*; 1988; vol. 31, No. 2; pp. 100–103.

Giokas, William J.; "Applications of Smaller Diameter Circular Knits"; Mar. 13–15, 1991; ppg. 1–8.

Maryland Speciality Wire, Inc.; "Weaving Wire, Braiding Wire, Lashing Wire, Knitting Wire"; ppg. 4–5.

*Primary Examiner*—Bruce Snow
(74) *Attorney, Agent, or Firm*—Richard J. Godlewski

(57) ABSTRACT

A prosthetic device for sustaining a vessel or hollow organ lumen (a stent) having a tubular wire frame (1) with rows of elongate cells (2) each having a larger axis and a smaller axis. The cells are arranged with the larger axis in the circumferential direction of the frame (2) and the smaller axis parallel to the axial direction thereof. Each cell is formed by two U-shaped wire sections, and in a plane perpendicular to the longitudinal axis one of the branches of the U-shaped wire sections in one row form together a closed ring shape (4) which provides the frame (1) with large radial stiffness. In the axial direction the frame (1) has only low stiffness so that it easily conforms to the vascular wall even if this deforms due to external loads. The interconnection between the cells (2) may be flexible.

23 Claims, 6 Drawing Sheets

U.S. PATENT DOCUMENTS

| | | |
|---|---|---|
| 5,234,457 A | 8/1993 | Anderson |
| 5,370,683 A | 12/1994 | Fontaine |
| 5,382,259 A | 1/1995 | Phelps et al. |
| 5,643,339 A * | 7/1997 | Kavteladze et al. ........... 623/1 |
| 5,800,519 A | 9/1998 | Sandock |
| 6,336,938 B1 * | 1/2002 | Kavteladze et al. ....... 623/1.15 |
| 6,383,216 B1 * | 5/2002 | Kavteladze et al. ....... 623/1.22 |

* cited by examiner

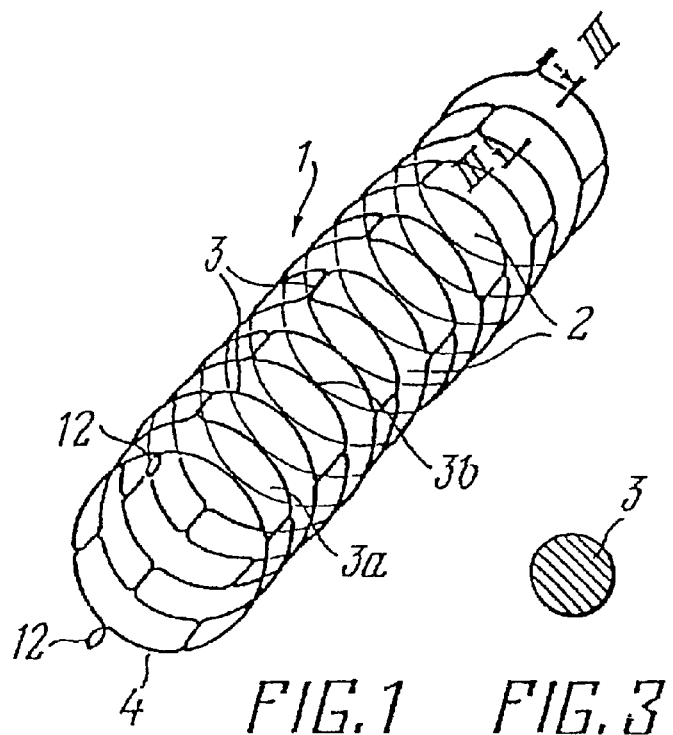
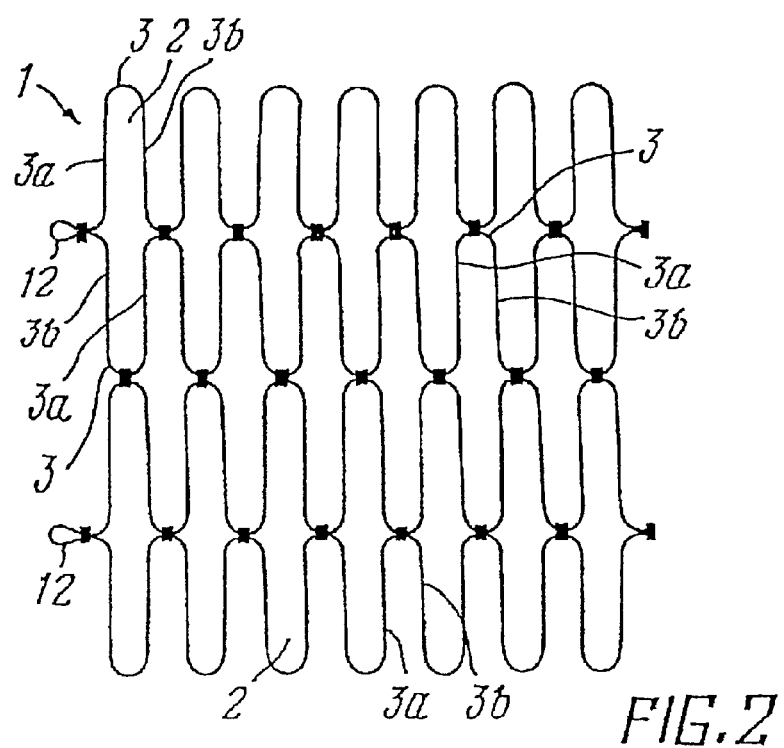
FIG.1  FIG.3
FIG.2

IMPLANTABLE, SELF-EXPANDING PROSTHETIC DEVICE

CROSS-REFERENCE TO RELATED APPLICATIONS

This application is a continuation of U.S. Utility patent application Ser. No. 09/645,179, filed Aug. 24, 2000, now U.S. Pat. No. 6,383,216, which is a continuation of U.S. Utility patent application Ser. No. 08/450,009, filed May 25, 1995 now U.S. Pat. No. 6,336,938, which is a continuation-in-part of U.S. Design patent application Ser. No. 29/034, 346, filed Feb. 2, 1995, now U.S. Design Patent No. D380, 831 entitled "An Implantable, Self-Expanding Stent" and commonly assigned herewith, which application is a continuation-in-part of U.S. Utility patent application Ser. No. 08/379,582, filed Feb. 1, 1995, now U.S. Pat. No. 5,643,339 entitled "A Prosthetic Device for Sustaining a Blood Vessel or Hollow Organ Lumen," which application is the U.S. national phase of International Patent Application No. PCT/DK93/00256, filed Aug. 6, 1993, which application claims priority to Russian Application No. 5057852, filed Aug. 6, 1992 (now Reg. No. 35-13-426, granted Feb. 18, 1993).

TECHNICAL FIELD

The invention pertains to implantable medical devices and, in particular, to a self-expanding prosthetic device for sustaining a vessel or hollow organ lumen.

BACKGROUND OF THE INVENTION

Various diseases of blood vessels or hollow organs cause a stenosis or complete obturation (occlusion) of their lumen, which results in a decrease or complete loss of their functional attributes. The wide spread of diseases of this kind demands an elaboration of quite new methods of medical treatment.

Devices for sustaining a blood vessel or hollow organ lumen typically have a tubular shaped frame body which is introduced in the vessel or hollow organ and fixed in the necessary place to sustain its lumen. The problem of designing such devices has already a twenty year history. Nevertheless, a universally reliable device satisfying all necessary requirements has as yet not been created.

A device for sustaining a vessel or hollow organ lumen should satisfy the following requirements:

effectively fulfill the function of recovering and sustaining the vessel or hollow organ lumen;

have a reliable and simple delivery control system;

have a wide range of sizes from 3 to 50 mm and more;

have biological compatibility with organism tissues;

be useable in different anatomical areas of vessels and hollow organs;

cause minimum trauma during and after operation; and have a stiff construction to counteract in situ external compression forces.

An attempt to create a device compatible with tissues was undertaken in USSR Patent No. 1237201, dated Feb. 15, 1986. This known device for sustaining the vessel or hollow organ lumen represents a wire frame having a tubular shaped body. The frame is formed by a wire element, having round or square cross-section and arranged in a cylindrical helical line. The frame has a shape of a helical cylindrical spring and it is furnished with fixing elements to keep it on the device for delivery into the vessel or hollow organ. Each fixing element is made in the form of a loop, one of which is formed at the initial section of the wire element, and the other at its final section. The facility for delivering the above device to a vessel or hollow organ comprises an introducer in the form of an X-ray contrast tube and another X-ray contrast tube of a lesser diameter, on whose surface the device is secured by means of a connecting element. The material of the frame wire is an alloy of the titanium-nickel system, which is biologically compatible with the organism tissues.

The device known from the USSR patent is reliable in use. However, it is expedient to use the known device in vessels or hollow organs having a diameter of not more than 8 mm, which is conditioned by the value of the ultimate strain of the frame material limited by 8% (the so-called strain limit of shape memory effect), as well as by the demand of minimizing the puncture hole (hole in vessel through which the device is introduced into an organ). Furthermore, the device can withstand only limited external compression forces.

The use of the known device in vessels and hollow organs with a diameter exceeding 8 mm, and without exceeding the ultimate strain of the frame material, would demand a decrease of the thickness of the wire frame elements, which would result in a further loss of stiffness of the frame. Alternatively, it would be necessary to increase the diameter of the puncture hole, which in turn would cause intolerable trauma to the vascular or hollow organ walls. Thus, the mentioned construction of the device for sustaining a vessel or hollow organ lumen is applicable only for vessels or hollow organs whose diameter is less than 8 mm, which sharply narrows the field of its application.

The execution of the function of effectively recovering and sustaining a vessel or hollow organ lumen by the described device demands an arrangement of the coils of the wire frame with a minimum lead to prevent germination of atherosclerotic patches, or counteract the occlusion. However, the making of the frame with a minimum lead between coils results in a loss of its stiffness in the vessel or hollow organ. As a result, external compression forces effect a change of the frame's arrangement in the vessel, i.e., the frame's longitudinal axis gets arranged at an angle to the vessel axis, or in an increase of the lead between coils. Both in the first and second cases, the frame stops functioning, and the vessel or hollow organ lumen gets reduced.

As it was described above, the frame is furnished with fixing elements on the front and rear ends. The fixing elements are made in the form of loops lying in the plane perpendicular to the frame axis in such a manner that the partial overlapping of the frame lumen occurs. As a result, turbulent flows in the blood current are formed and facilitate the appearance of various complications such as atherosclerotic formations.

The described facility of frame delivery is reliable enough in the process of introduction of the frame to the affected area. However, at installation of the frame with the aid of this facility one of the fixing loops gets released. The frame, being constrained in a reduced diameter until this moment, gets released and uncoils in the direction opposite to the direction of coiling at its fixing, acquiring its initial shape. In the process of uncoiling, which is uncontrolled, trauma to the vascular or hollow organ walls may occur, which has an unfavorable affect on the result of operation. In addition, the frame can occupy an arbitrary position in the vessel that is uncontrolled by the surgeon.

The described frame has the shape of a helical cylindrical spring. If we examine the frame section in a plane perpendicular to the frame axis and passing through the coil surface, it is seen that the frame coil located in the plane has a break, which decreases the frame stiffness under the effect of radially acting forces.

Another device for sustaining a vessel or hollow organ lumen is known (Ann Radiol, 1988, 31, n.2, 100–103), and it has a tubular shaped wire frame formed by a wire element, which in development represents a saw-tooth line. In order to permit a change in the stiffness of the frame, the latter is bound at the tops by a caprone thread.

The branches of the wire element are arranged along the longitudinal axis of the tubular frame, which provides for a constancy of the frame's linear dimensions at the delivery and installation of the frame in the affected place of the vessel or hollow organ. To fix the frame in the vascular or hollow organ walls, provision is made for fixing elements in the form of hooks.

In the described construction, use is made of materials whose ultimate elastic strain makes up tenths of a percent. The delivery system represents an X-ray contrast tube accommodating a pusher, which is a piston with a rod. For transportation (delivery), the device is placed in the X-ray contrast tube, and by means of the rod the surgeon acts upon the piston interacting with the device.

The described device has found a wide application for sustaining the lumen of the affected areas of veins, in which there are no atherosclerotic processes. The use of this device in arterial vessels is hardly possible because of the large distances between the wire elements, which may result in germination of atherosclerotic patches and, as a consequence, in an ineffective use of this device.

The latter known device is used for sustaining the lumen of the affected areas of veins whose diameter is within 15 to 30 mm. In this case, a wire of a large diameter is used to impart the necessary stiffness to the construction. If this device were to be used in smaller vessels or hollow organs having a diameter from 3 to 15 mm it would be necessary to decrease the wire thickness (diameter). However, the loss in diameter thickness may hardly provide an effective means for sustaining the lumen.

Due to the arrangement of the wire branches in the peripheral direction of the tubular frame body, the given construction is stable and has a high stiffness in the axial direction, which prevents full adjustment of the vessel geometry and may traumatize the vascular or hollow organ walls.

When it is necessary to deliver the above device to the affected area along a curved path, the elastic deformation of the frame wire elements changes into plastic deformation, which results in an irreversible change of the device shape. Thus, delivery of the given frame to the affected place is possible only along a path close to a straight line, which considerably narrows the number of the anatomical areas, where the frame could be used.

A device of the initially mentioned kind is known from EP-A-221570. In this device, the larger axis of each cell is arranged in the axial direction of the tubular body and the smaller axis in the circumferential direction thereof. The wire sections forming the cells are rigidly interconnected.

The delivery facility of the described device comprises an X-ray contrast tube with an inflatable balloon, on the outside of which the wire frame is located. To press the wire frame onto the X-ray contrast tube, provision is made for one more tube enveloping the frame on its external surface. In delivery of the frame to the affected area of the vessel or hollow organ, the external tube is removed, and the balloon is inflated so that the frame is expanded and acquires its final shape whereafter it interacts with the vascular walls. Then, the X-ray contrast tube is removed from the vessel, and the frame is installed in the affected area.

Its delivery and installation in the affected area is sufficiently reliable and convenient. However, the use of a rigid joint by fusing together, soldering or welding of the wire elements in the points of their intersection seems to be unreliable because of:

a probable proceeding of electrochemical processes in the soldering zone, which may cause damage to the joint, loss of stiffness in the frame and consequently, loss of its functional attributes; and formation of the so-called welding zone with an embrittled material structure, which may make this joint unreliable.

The described device can be used for sustaining the lumen of vessels or hollow organs within a range of sizes from 3 to 8 mm. In the described construction use is made of materials whose ultimate elastic strain makes up tenths of a percent. When it is necessary to deliver the device to the affected area along a curved path, a danger arises of exceeding the ultimate elastic strain and, consequently, the proceeding of the process of plastic deformation of the frame material. Thus, the delivery of the given frame is possible only along a path close to a straight line, which essentially decreases the possibility of its use in different anatomic areas. The known device has a large stiffness in the axial direction which may traumatize the walls of the vascular or hollow organ in the regions around the ends of the device if the device supports a vascular or hollow organ which changes its shape during adaptation to varying external loads. Further, it is a common disadvantage of the known devices that they possess limited radial stiffness, which allows them to support only vascular or hollow organs that are not surrounded by a bone structure taking up external loads.

SUMMARY OF THE INVENTION

The invention is based on the problem of creating a device for sustaining a vessel or hollow organ lumen, in which the shape and arrangement of cells forming the tubular frame provide the frame with a large stiffness in the radial direction and only low stiffness in the axial direction so that the device without risk of traumatization will keep the vascular or hollow organ open, even if the latter changes shape due to external loads.

This is obtained by a prosthetic device having a wire frame in the form of a flexible tubular shaped body which in development is formed by many rows of interconnected cells, each of which cells comprises two U-shaped wire sections forming together approximately an elongated oval with a larger axis and a smaller axis, wherein adjacent cells in neighboring rows are shifted by half of the larger axis of the oval with respect to each other in the direction of the larger axis and are shifted by the smaller axis of the oval with respect to each other in the direction of the smaller axis. According to the invention, the device is characterized in that the larger axis of the oval is directed in the circumferential direction of the tubular body and the smaller axis parallel to the axial direction thereof so that in a plane perpendicular to the longitudinal axis of the body one of the branches of the U-shaped wire sections in one row forms together a closed ring shape.

By arranging the cells so that the larger axis of the oval is directed in the circumferential direction the device has on one hand a large flexibility in the axial direction which allows the device to bend simultaneously with the vascular or hollow organ even if the bending is very localized because the long branches of the U-shape are easily deformed in the axial direction. In addition, the device is very rigid towards localized radial compression because the U-shaped branches of each row of cells form two circumferential rings having a relatively high stiffness in their plane. The flexibility of the device in the axial direction further ensures that a local deformation of the vessel does not cause the device to lengthen in the axial direction as the deformation is absorbed within the pressure affected rows of cells. This causes the device to stay fixed with respect to the surrounding supported wall of the vascular or hollow organ so that traumatization is avoided. Under the action of external compression force, the ring shape is essentially uniformly loaded. The axial stiffness of the device can to some extent be adjusted as needed by varying the cross-sectional area of the frame wire. By varying the number of cells in the frame, it becomes possible to select the optimum axial stiffness of the frame, so that the vascular or hollow organ wall is traumatized as little as possible.

In a preferred embodiment, adjacent cells in one row are interconnected in a flexible manner at the axially extending portion of the U-shaped wire sections. The flexible interconnection allows large deformations of the initially unloaded cell geometry without large deformations in the wire proper because the wire sections are not rigidly fixed to each other.

When the device is to be introduced, the ends of the tubular frame are pulled away from each other and the frame diameter is reduced until the frame can be inserted into a delivery catheter. During lengthening of the frame, the major portion of cell deformation occurs in the long branches of the wire sections, and it is assumed that the axially extending portion of the U-shaped wire sections is only slightly deformed so that the entire U-shaped wire section is substantially uniformly loaded. Consequently, the diameter of the tubular frame may be drastically reduced during insertion without exceeding the elastic strain limit of the wire material. This makes it possible to use devices according to the invention within a wide range of sizes and to introduce the devices through a small puncture hole in the patient, even if the wire is made of, e.g., stainless steel.

Preferably the flexible interconnections are accomplished by winding the axially extending portions around each other, more preferably so that the one wire portion is wound only one turn around the associated wire portion. During deformation of the U-shaped wire sections, the windings may move apart and/or open which reduces strain in the wire. The wound wire portions also act as a kind of hinge joint allowing the two U-shaped wire sections in a cell to swivel with respect to each other when the frame is radially loaded. The wound flexible interconnections present a further advantage, namely that as an alternative to axially lengthening of the frame prior to insertion in the catheter the tubular frame may be twisted about its longitudinal axis by turning the two frame ends in opposite directions. This causes the wound interconnections to open and the frame to collapse to a reduced diameter allowing insertion. When the frame after positioning abreast of the site to be supported is pushed out of the catheter it "uncoils" to its initial diameter without any substantial axial shortening of the frame, which leads to an uncomplicated and very precise positioning of the device in the vascular or hollow organ.

In a further embodiment, which is preferred due to its simplicity of manufacture, the device is characterized in that each U-shaped wire section is composed of two separate wires each of which runs helically through the rows of cells, and that the two wires are wound, preferably, one turn around each other at the axially extending portion where they meet to form the bottom leg of the U-shape.

The device may have wires of a shape memory alloy exhibiting thermally activated shape memory properties, preferably a nickel-titanium alloy, but more preferably the wires are of a shape memory alloy exhibiting superelastic properties, advantageously a nickel-titanium alloy. Such a shape memory alloy can be excessively deformed and yet return to its set predetermined shape without loss of stiffness or introduction of permanent deformations in the wire. The shape memory alloy wire frame can be reduced to a diameter of only a few mm during insertion irrespective of its unloaded diameter which, e.g., may be as large as 50 mm so that the frame can be introduced into the patient through a single small diameter catheter requiring only a small puncture hole in the patient. The superelastic alloy is preferred in order to avoid thermal control during insertion. When this alloy is deformed it exhibits stress induced martensite.

The above-described possibilities of variation of the axial and radial stiffness of the frame allow the latter to fulfill the function of sustaining a vessel or hollow organ lumen within any range of their standard sizes, for example, from a diameter of 3 mm to a diameter of 50 mm, and be applicable in different anatomical areas of the vessel or hollow organ and even to be introduced along a tortuous path. The device may also be used for retention of blood clots as a Vena cava filter.

The aforementioned prosthetic device of the present invention has been described with the flexible interconnections all being wound in either a clockwise or counterclockwise direction. Although well suited for its intended purpose, the stent with its flexible interconnections all wound in the same direction exhibits a twisting, spiraling, corkscrewing, or uncoiling motion as it is deployed from the end of a delivery catheter or tube. This uncoiling motion was previously described and is undesirable in that plaque or other material formed on the wall of a vessel can be dislodged with undesirable trauma occurring to the patient. By way of example, this trauma could result in the formation of an embolism and resultant patient death. To minimize, if not eliminate this undesirable motion, the flexibly interconnected wire segments of the stent are selectively wound in opposite directions to effectively counterbalance the stent.

In one embodiment of the present invention, the flexibly interconnected wire segments of the cells in each row are all wound in the same direction, whereas the wire segments of the cells in an adjacent row are all wound in an opposite direction. This advantageously counterbalances the moments formed by the flexibly interconnected wire segments around and along an adjacent pair of rows. Furthermore, the winding of the wire segments in this manner forms a uniformly shaped wall with a minimum wall thickness.

In another embodiment of the present invention, the flexibly interconnected wire segments in each cell are wound in opposite directions to counterbalance the moments formed in the cell. As a result, the flexibly interconnected wire segments in each cell and row of the stent are advantageously counterbalanced. Adjacent loops at one end of the stent as well as fixedly secured, adjacent wire segments at an other end of the stent are also wound in opposite directions to further advantageously counterbalance the stent.

BRIEF DESCRIPTION OF THE DRAWING

In the following description, examples of embodiments of the device according to the invention are described in further detail with reference to the schematic drawings, in which FIG. 1 shows a perspective view of the device for sustaining a vessel or hollow organ lumen, according to the invention;

FIG. 2 shows in a larger scale, a development of the frame surface;

FIG. 3 is a section after line III—III in FIG. 1;

DETAILED DESCRIPTION

Figure 4:
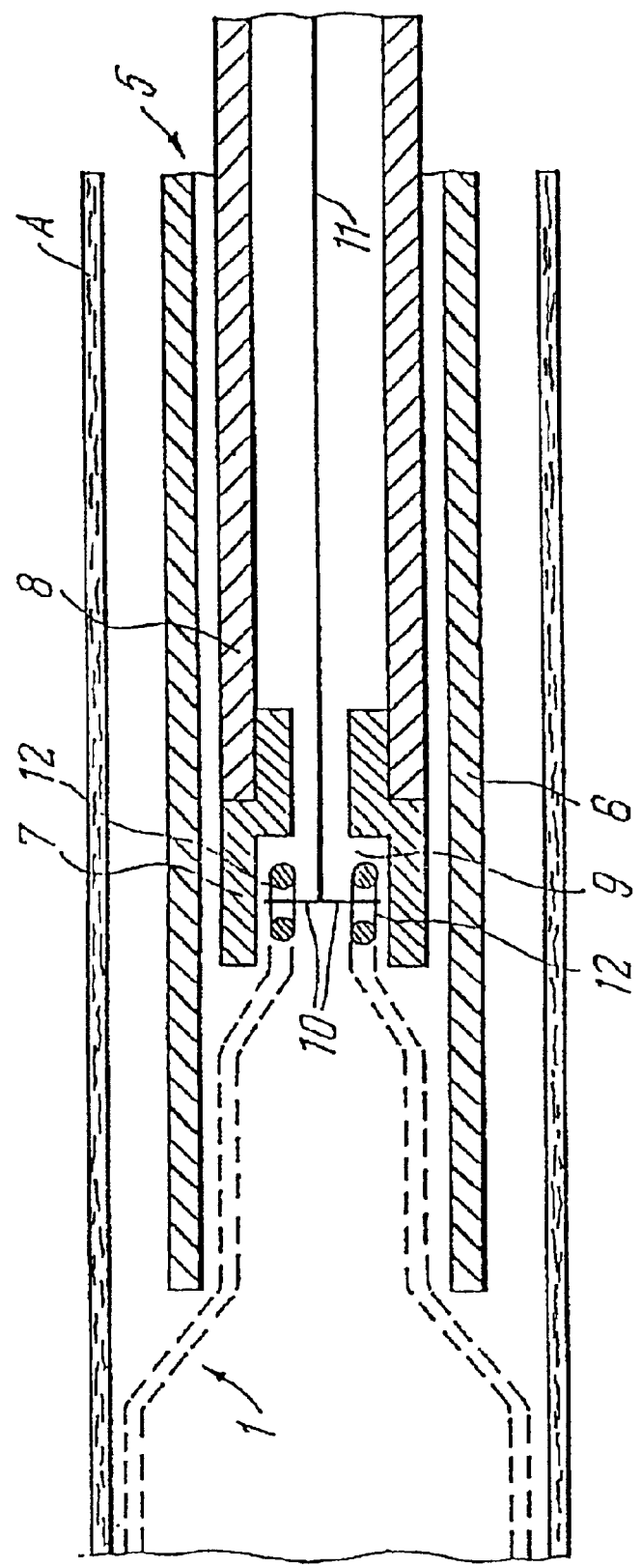
FIGS. 4 and 4a illustrate the delivery device with the frame in longitudinal section and perspective view, respectively.

The device for sustaining the lumen, for example of the femoral artery, accomplished in accordance with the invention, has wire frame 1 in the form of a tubular shaped body such as a hollow cylindrical body.

The cylindrical surface of frame 1 shown in development in FIG. 2 is formed by a large number of interconnected cells 2 formed by two U-shaped wire sections 3, interconnected by their branches 3a, 3b, and forming approximately an oval, whose larger axis is arranged in the circumferential direction of the body and the smaller axis parallel to its axial direction. Cell 2 of each subsequent row is shifted in the circumferential direction with respect to cell 2 of the present row by ½ of the length of the oval larger axis. Each branch 3a or 3b of the U-shaped wire section 3 belongs to two cells 2 in adjacent rows, except for the first and last rows. In a cross-section of frame 1 in a plane perpendicular to its longitudinal axis and passing through the long branches of the U-shaped wire sections 3 of one row these branches form a closed ring shape 4 which provides the frame with large stiffness in a radial direction and ensures that the cell will only to a very limited extent be deformed in the axial direction when it is radially loaded. The wire section 3 may have a circular cross-section as seen in FIG. 3.

The wire can be made of a titanium-nickel alloy having shape memory properties which may either be thermally or stress activated. When the wire is of such an alloy which may be heavily deformed without permanent deformation of the wire, the cells 2 of frame 1 can be interconnected by a rigid joint at the tops of the U-shaped wire sections. Alternatively the U-shaped sections may be flexibly interconnected by small rings, e.g., of thread.

The described device is introduced into the vessel A such as the femoral artery as follows. A delivery device 5 comprises a hollow X-ray contrast tube 6, containing a hollow pusher 7 with a rod 8. The pusher 7 has an internal space 9 including two stops 10 in the form of cylindrical radially extending pins rigidly connected with a holder 11 arranged along the longitudinal axis of rod 8. The distance between the extreme points of stops 10 essentially corresponds to the inside diameter of pusher 7. The holder 11 is installed with a possibility of longitudinal displacement.

The frame 1 is secured to the stops 10 of holder 11 by means of lugs 12 inserted over the stops 10. The holder 11 connected to frame 1, is fixed with respect to rod 8. The rod 8 is introduced into X-ray contrast tube 6 simultaneously with the frame 1 being drawn into contrast tube 5 along its longitudinal axis. When entering the contrast tube 6 the sections 3 forming frame 1 acquire a shape close to a straight line and the frame diameter is reduced to a few mm. The forward end of contrast tube 6 is then, through the puncture hole, brought to the affected area of vessel A. Frame 1 may alternatively be brought into tube 6 by rotating holder 11 with respect to the frame end opposite to the end fixed to stops 10 so that the frame 1 is collapsed to a small diameter and may be inserted into tube 6.

When the delivery device 5 is in position in the vessel or hollow organ the surgeon, while acting upon frame 1 through rod 8, withdraws the X-ray contrast tube from the frame so that the wire sections 3 of the device fold out to the original tubular shape.

If the wire is a thermally activated shape memory alloy, the blood temperature heats the wire and the device acquires its initial shape. If the wire is superelastic, it will simply return to its preset shape when the restraining force from tube 6 is removed.

Figure 4A:
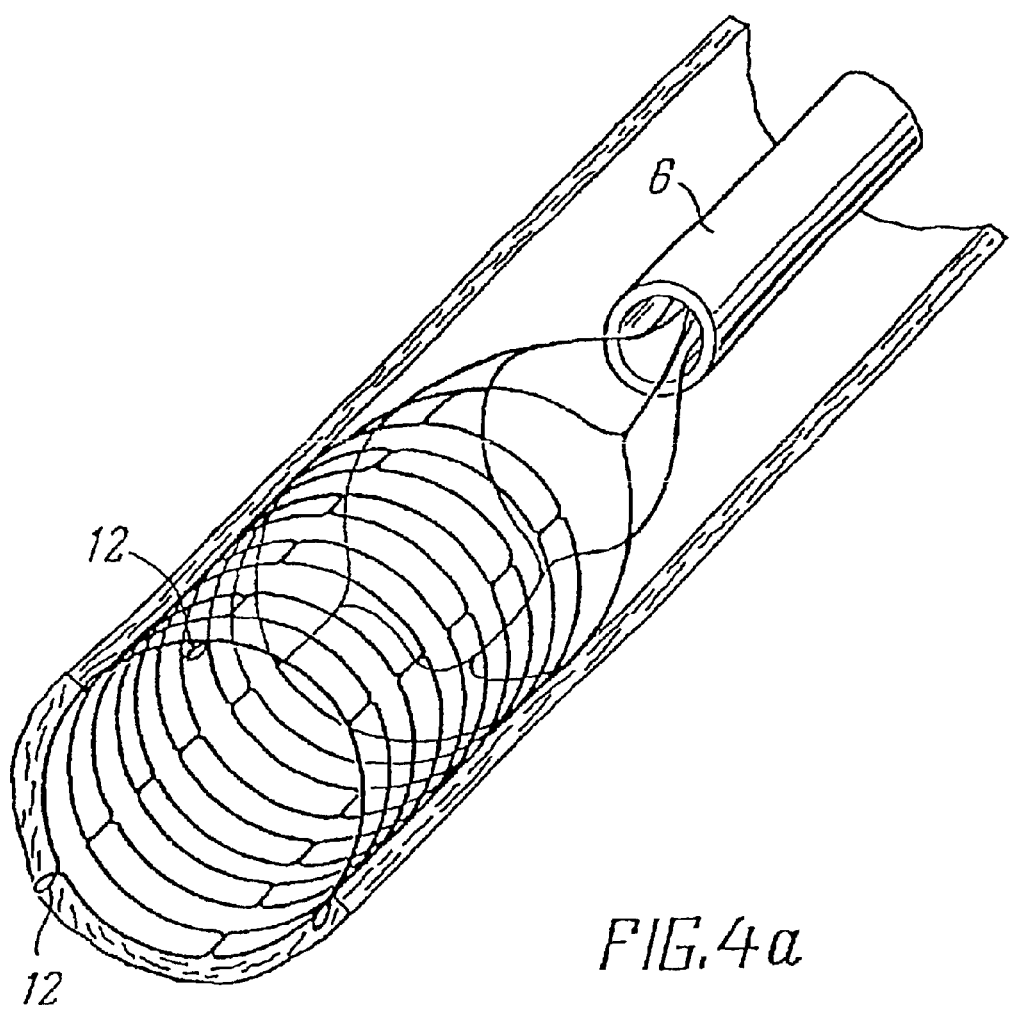

Recovery of the initial frame shape occurs in succession by forming closed ring-shaped circuits 4 in the plane perpendicular to the device axis. The ring-shaped circuit interacts with the walls of vessel or organ A (FIG. 4a), sustaining its lumen constant and repeating its geometry due to the maximum radial stiffness and optimum axial stiffness of frame 1 (FIG. 1). The described constructional features of the device make it possible to bring it to the affected area through a minimum puncture hole.

Figure 5:
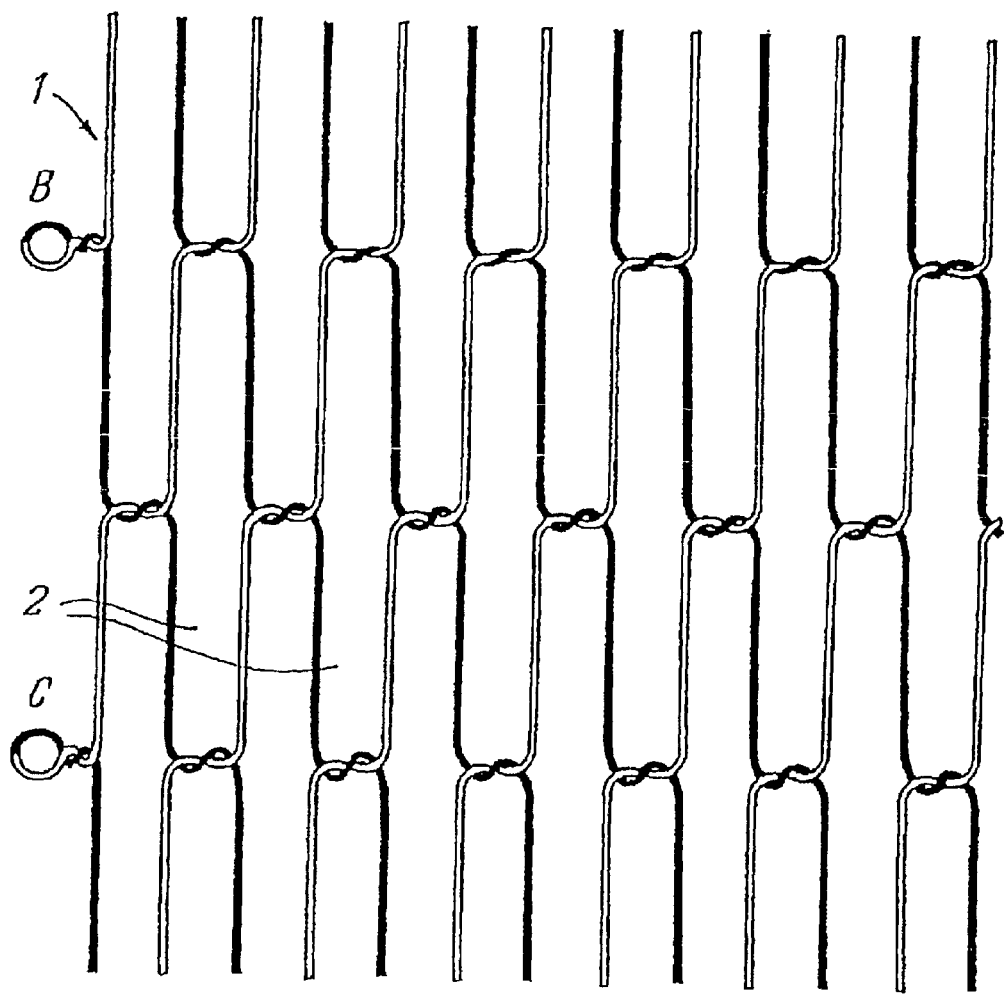
FIG. 5 shows in development a section of the frame surface in a second embodiment according to the invention, in large scale.

The embodiment shown in FIG. 5 has cells 2 of similar shape as in the above described embodiment, but the cells are interconnected in an alternative manner. Each U-shaped wire section is composed by two different wires which run in a substantially helical shape or helically through the rows of cells and the wires and are wound one turn around each other at the axially extending wire portion where they meet to form the bottom portion or leg of the U-shape. At the ends of the frame, the associated pairs of wires are joined at points B and C by twisting the wires around each other. The formed loop can be bent into the adjacent outer cell in order not to traumatize the vascular wall. The formed interconnections between the cells are highly flexible, and the wires can deform more or less independently of each other.

The device is introduced into the hollow vein, artery or organ A in the same manner as the above described device.

The device, preserving a constant diameter for the vessel lumen and maintaining or reinstating its geometry, has an increased durability because of the movable joint between the wires.

The accomplished analysis and the obtained positive estimate of the biological compatibility of the described device made it possible to perform bench tests. The mechanical characteristics of the device were studied on a special model of the arterial system of a human being, and the technical elements of the procedure of its implantation in different areas of the vascular channel were elaborated.

The bench tests have displayed good qualities of the described device and made it possible to conduct experimental investigations on animals.

Experiments were conducted on 10 dogs, 3 of them were subjected to an acute experiment, and 7 were subjected to dynamic observations. Implantations were accomplished into the thoracic, abdominal aortas, renal, iliolumbar and femoral arteries. During X-ray analyses, it was generally noted that the devices did not shift from the places of their initial implantation, the device shape conforms to its initial one, and no symptoms of thrombosis or stenosis of the vessel were revealed.

Figure 6:
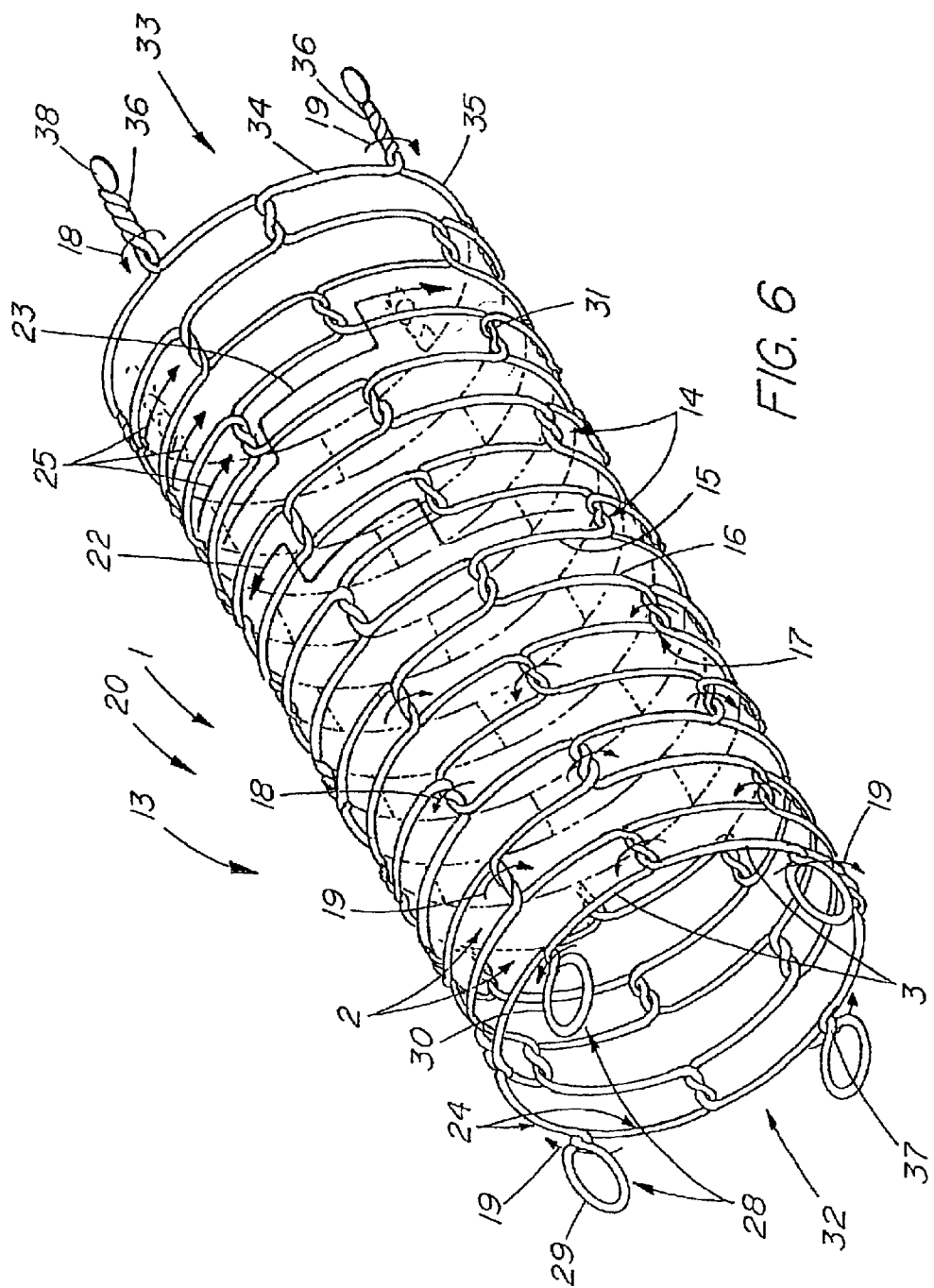
FIG. 6 depicts a pictorial view of a third embodiment of the present invention.

FIG. 6 depicts a pictorial view of another embodiment of the present invention. In this embodiment, prosthetic device 20 is an implantable, self-expanding stent and includes a wire frame 1 having a flexible tubular shape 13 and a plurality or, more particularly, rows 25 of interconnected cells 2 with flexible interconnections 14. The stent is depicted in an expanded condition with four flexibly interconnected cells forming a row and extending around the circumference of the stent. Each cell has first and second substantially U-shaped wire sections 3. Each U-shaped wire section 3 includes first and second flexibly interconnected wire segments 15 and 16 each of which runs in a stair-step manner helically along the wire frame and through the rows of the interconnected cells. The flexibly interconnected wire segments are wound around each other at an axially extending portion 17 of the wire frame and form the flexible interconnections of each cell as well as the U-shaped wire sections of the cells. To specifically address the uncoiling problem of the prosthetic device or stent when the stent is released from the delivery tube 6 and into a vessel or hollow organ lumen, the flexible interconnections 14 or, more particularly, flexibly interconnected wire segments 15 and 16 in each U-shaped wire section of a cell are wound in opposite, counterclockwise and clockwise directions 18 and 19. The oppositely wound flexible interconnections in each cell of a given row not only counterbalance the twisting moments created by the flexible interconnections in each cell, but also counterbalance the twisting moments created in the row of interconnected cells.

To further minimize, if not eliminate, the twisting or uncoiling motion of the stent when being released from the delivery tube, each of the first and second wire segments in a pair 24 runs in a stair-step manner helically along the wire frame and through the interconnected cells thus extending through the flexible interconnections of at least two nonadjoining ones of the cells and, as shown, extend from the first wire frame end to the second. This stair-step helical configuration is also shown in FIG. 5. However, returning to FIG. 6, wire segment 15 runs in a counterclockwise helical direction 22, whereas wire segment 16 runs in an opposite, clockwise helical direction 23. As indicated, first and second wire segments 15 and 16 are grouped in pairs 24. As a result, the number of wire segments running helically in a counterclockwise direction are equivalent in number to the wire segments running helically in a clockwise direction, thereby counterbalancing each other. To further counterbalance the stent, the pairs of wire segments are also even in number as depicted in stent 20 of FIG. 6.

The prosthetic device and, in particular, stent 20 also includes at one end 32 an even number of loops 28. A pair 24 of first and second wire segments 15 and 16 extend from each loop. By way of example, a separate piece of wire about its midpoint is bent around a cylindrical peg to form a loop 28 and a pair 24 of first and second wire segments 15 and 16. The wire segments are wound a half turn and then around a cylindrical mandrel in a stair-step manner and a helical direction to form the stent. In this example, stent 20 includes four loops of which two opposing loops are wound in counterclockwise direction 18, and the adjacent opposing loops are wound in clockwise direction 19. This is done to maintain the stent in a counterbalanced condition around its circumference. At opposite end 33 of the stent, pairs 36 of first and second wire segments 34 and 35 are wound together and fixedly secured to each other with a weld or solder bead 38. Four or five turns are made at end 33 of the stent so that the flexible interconnection of the wire segments is maintained in the vicinity of the last row of cells Furthermore, the four or five turns of the wire segments provide a buffer for the flexible interconnection due to the deterioration of the superelastic or shape memory property of the wire material when solder or weld beads 38 are formed. Adjacent pairs of fixedly secured wire segments 34 and 35 are wound in opposite directions 18 and 19.

As previously suggested, first and second flexibly interconnected wire segments are wound in opposite directions at the laterally extending portions of each U-shaped cell. As depicted in stent 20 of FIG. 6, all the flexible interconnections forming a laterally extending column of the stent are wound only one turn and alternate in direction every second row.

Figure 7:
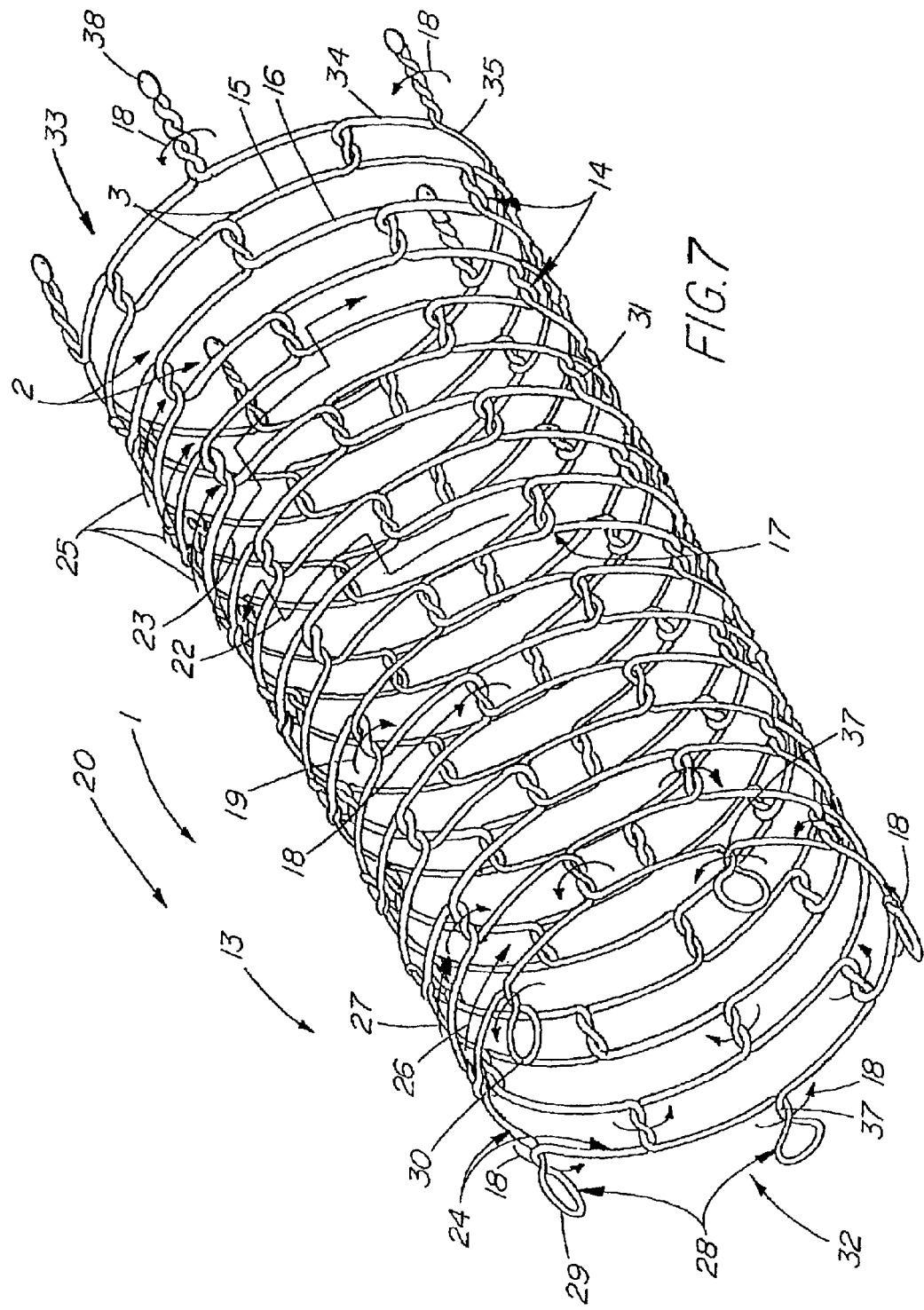
FIG. 7 depicts a pictorial view of a fourth embodiment of the present invention.

FIG. 7 depicts yet another preferred embodiment of the present invention. In this preferred embodiment, prosthetic device or stent 20 includes a wire frame 1 having a flexible tubular sheath 13 and rows 25 of interconnected cells 2. Each of the cells has first and second substantially U-shaped wire sections 3, wherein each substantially U-shaped wire section includes first and second flexibly interconnected wire segments 15 and 16. Each of the flexibly interconnected wire segments runs helically along the wire frame in a step-like manner and through the interconnected rows of cells thus extending through the flexible interconnections of at least two nonadjoining ones of the cells and, as shown, extend from the first wire frame end to the second. The flexibly interconnected wire segments and each U-shaped wire section are wound around each other one turn at axially extending wire portion 17 of the frame. As previously suggested, one or more of the U-shaped wire sections are wound in counterclockwise direction 18, while at least others of the wire sections are wound in a clockwise direction 19 opposite to direction 18. Unlike the cells of stent 20 of FIG. 6, all the U-shaped wire sections in, for example, row 26 of interconnected cells are wound in counterclockwise direction 18. To circumferentially and longitudinally counterbalance row 26, all the U-shaped wire sections in adjacent row 27 of interconnected cells are wound in clockwise direction 19.

To maximize the radial strength of the stent, the long branches of U-shaped wire sections 3 are formed in a closed ring shape 4, that is contained in a plane perpendicular to the longitudinal axis of the stent. The wire of the stent is preferably a nickel-titanium alloy having shape memory and superelastic properties. Preferably, the transformation temperature of the nickel-titanium alloy is selected to be below the normal temperature of a human body, whereby the alloy is in an austenitic state exhibiting its superelastic property. After the stent is formed, typically around a cylindrical mandrel, the fully deployed tubular shape of the nickel-titanium alloy stent is heat set in a well-known manner at a temperature typically well above its transformation temperature. Once heat set, the stent wants to return to its fully deployed tubular shape after being, for example, stretched or elongated for insertion in a delivery tube or catheter. However, in the fully deployed tubular shape, the branches of each U-shaped wire section are in a plane perpendicular to the longitudinal axis of the stent, which provides maximum radial strength for the stent. Each of flexible interconnections 14 is positioned at an axial portion 17 of the wire frame and functions as a flexible hinge when the diameter of the stent is being either expanded or contracted. The flexible hinge is formed by winding the first and second wire segments only one turn 31 around each other.

Similar to the previously described embodiments, stent 20 of FIG. 7 also includes at one end 32 a plurality of loops 28 from each of which extends a pair 24 of flexibly interconnected wire segments 15 and 16. Each loop is formed by winding wire segments 15 and 16 only half a turn 37. This maintains the flexible interconnection of the segments as well as a counterbalance with the flexible interconnections that extend axially along the length of the stent. In this embodiment, the five loops of the stent are all wound in a counterclockwise direction 18. However, adjacent loops, such as 29 and 30, can be wound in counterclockwise and clockwise directions 18 and 19 around the circumference of the stent. This alternate loop winding direction is preferred where the loops or pairs of flexible wire segments are even in number.

At an other end 33 of the stent, flexibly interconnected wire segments 34 and 35 are fixedly secured to each other with, for example, a well-known solder or weld bead 38. In this embodiment of the stent, the fixedly secured wire segments are all wound in counterclockwise direction 18. An even number of pairs can be wound in opposite counterclockwise and clockwise directions to further facilitate counterbalancing of the stent.

The flexibly interconnected wire segments in each U-shaped wire section of a given row are all wound in the same direction, whereas wire segments in each U-shaped wire section of an adjacent row are wound in an opposite direction. This provides counterbalancing of the flexibly interconnected wire segments longitudinally along pairs of adjacent rows. Although the wire segments are not counterbalanced in each row, the wall thickness of the stent along its length is uniform with a low profile, thus contributing to the desirability of this configuration.

It is to be understood that the above-described prosthetic device is merely an illustrative embodiment of the principles of this invention and that other devices or stents may be devised by those skilled in the art without departing from the spirit and scope of this invention. In particular, it is fully contemplated that the flexible interconnections of the stent can be formed with any number thereof in either the counterclockwise or clockwise directions. At a minimum, one flexible interconnection need be wound in a given direction with the remaining interconnections being wound in the opposite direction. The number of flexible interconnections in opposite directions is only limited by the amount of twisting, spiraling, corkscrewing, or uncoiling of the stent that is clinically acceptable to the attending physician. However, the amount of twisting, corkscrewing, spiraling or uncoiling motion of the stent should be minimized so as to reduce the risk of shearing or cutting plaque from the wall of, for example, a blood vessel. Such twisting, corkscrewing, spiraling, or uncoiling motion of the stent can also cause trauma to delicate or fragile blood vessels, ducts, and the like.

What is claimed is:

1. A prosthetic device for sustaining a blood vessel or hollow organ lumen, comprising:
   a self-expanding wire frame having a flexible tubular shape and a plurality of first and second wire segments,
   the plurality of first and second wire segments having flexible interconnections and defining a plurality of cells, with each of the flexible interconnections being defined by a respective first wire segment and a respective second wire segment being wound about each other, and
   selected of the first wire segments extending through the flexible interconnections of at least two nonadjoining ones of the cells, and selected of the second wire segments extending through the flexible interconnections of at least two nonadjoining ones of the cells, wherein the flexible interconnections between adjoining cells extend axially along the wire frame, and wherein the first wire segments extend in step-wise fashion from a first end of the wire frame to a second end in a counterclockwise direction about the circumference of the tubular shape and the second wire segments extend in step-wise fashion from the first end of the wire frame to the second end in a clockwise direction about the tubular shape.

2. The prosthetic device of claim 1 wherein a respective first wire segment and a respective second wire segment are wound about each other at least one complete turn, to define a said flexible interconnection.

3. The prosthetic device of claim 1 wherein each of the first and second wire segments extends from the first end of the wire frame to the second end thereof.

4. A prosthetic device for sustaining a blood vessel or hollow organ lumen, comprising:
   a self-expanding wire frame having a flexible tubular shape and a plurality of first and second wire segments,
   the plurality of first and second wire segments having flexible interconnections and defining a plurality of cells, with each of the flexible interconnections being defined by a respective first wire segment and a respective second wire segment being wound about each other, and
   selected of the first wire segments extending through the flexible interconnections of at least two non-adjoining ones of the cells, and selected of the second wire segments extending through the flexible interconnections of at least two non-adjoining ones of the cells, wherein the first wire segments extend in step-wise fashion from a first end of the wire frame to a second end in a counterclockwise direction about the circumference of the tubular shape and the second wire segments extend in step-wise fashion from the first end of the wire frame to The second end in a clockwise direction about the tubular shape, and wherein the first and second wire segments in at least one of the flexible interconnections being wound in a first direction and the first and second wire segments in at least an other of the flexible interconnections being wound in a second direction opposite to the first direction.

5. The prosthetic device of claim 1 wherein each cell of one circumferentially extending row of cells is bounded longitudinally by a pair of the flexible interconnections that are wound in a common direction different from the direction in which are wound a pair of the flexible interconnections of the cells of the adjacent rows.

6. The prosthetic device of claim 1 wherein the flexible interconnections wound in a clockwise direction are substantially equivalent in number to the flexible interconnections wound in a counterclockwise direction.

7. The prosthetic device of claim 1 wherein the first and second wire segments comprise an even number of pairs.

8. The prosthetic device of claim 1 wherein the first and second wire segments are of a superelastic material.

9. The prosthetic device of claim 1 wherein the first and second wire segments are of a shape memory material.

10. The prosthetic device of claim 1 wherein the first and second wire segments are heat set.

11. The prosthetic device of claim 1 wherein the first and second wire segments are of a nickel-titanium alloy.

12. The prosthetic device of claim 1 wherein the wire frame includes at least tour discrete wire lengths each with a first half defining a first wire segment and a first end and a second half defining a second wire segment and a second end.

13. The prosthetic device of claim 12 wherein the first and second wire segments of each of the discrete wire lengths are integrally joined at one of the first and second ends of the wire frame, and first ends of the discrete wire lengths are fixedly joined to second ends of adjacent ones of the discrete wire lengths at the other of the first and second ends of the wire frame.

14. The prosthetic device of claim 13 wherein the first ends of the discrete wire lengths are wound about second ends of adjacent ones of the discrete wire lengths by being wound in a common direction.

15. The prosthetic device of claim 13 wherein the first ends of the discrete wire lengths are wound about second ends of adjacent ones of the discrete wire lengths with adjacent ones of the wound wire ends being wound in opposed directions.

16. The prosthetic device of claim 13 wherein the first and second wire segments of each of the discrete wire lengths form open loop where they are integrally joined.

17. The prosthetic device of claim 13 wherein the wire frame includes five discrete wire lengths.

18. The prosthetic device of claim 13 wherein the wire frame includes four discrete wire lengths.

19. The prosthetic device of claim 1 wherein at least one of the first wire segments and at least one of the second wire segments each being portions of a respective single length of wire.

20. A prosthetic device for sustaining a blood vessel or hollow organ lumen, comprising:
a wire frame having a flexible tubular shape and being comprised of a plurality of first and second wire segments,
the plurality of first and second wire segments having flexible interconnections and defining a plurality of cells, with each of the flexible interconnections being defined by a respective first wire segment and a respective second wire segment being wound about each other, and
selected ones of the plurality of first and second wire segments extending from a first end of the wire frame to a second end thereof, wherein the first wire segments extend in step-wise fashion from the first end of the wire frame to the second end in a counterclockwise direction about the circumference of the tubular shape and the second wire segments extend in step-wise fashion from the first end of the wire frame to the second end in a clockwise direction about the tubular shape.

21. A prosthetic device for sustaining a blood vessel or hollow organ lumen, comprising:
a wire frame having a flexible tubular shape and being comprised of a plurality of first and second wire segments,
the plurality of first and second wire segments having flexible interconnections and defining a plurality of cells, with each of the flexible interconnections being defined by a respective first wire segment and a respective second wire segment being wound about each other, and
the flexible interconnections between adjoining cells extending axially along the wire frame, wherein the first wire segments extend in step-wise fashion from a first end of the wire frame to a second end in a counterclockwise direction about the circumference of the tubular shape and the second wire segments extend in step-wise fashion from the first end of the wire frame to the second end in a clockwise direction about the tubular shape.

22. A prosthetic device for sustaining a blood vessel or hollow organ lumen, comprising:
a wire frame having a flexible tubular shape and a plurality of first and second wire segments each of which extend from a first end of the wire frame to a second end thereof,
at least one of the first wire segments and at least one of the second wire segments each being portions of a respective single length of wire,
the plurality of first and second wire segments having flexible interconnections and defining a plurality of cells, with each of the flexible interconnections being defined by a respective first wire segment and a respective second wire segment being wound about each other at least one complete turn with the flexible interconnections between adjoining cells extending axially along the wire frame, and
each of the first wire segments extending through the flexible interconnections of at least two nonadjoining ones of the cells, and each of the second wire segments extending through the flexible interconnections of at least two nonadjoining ones of the cells, wherein the first wire segments extend in step-wise fashion from the first end of the wire frame to the second end in a counterclockwise direction about the circumference of the tubular shape and the second wire segments extend in step-wise fashion from the first end of the wire frame to the second end in a clockwise direction about the tubular shape.

23. A prosthetic device for sustaining a blood vessel or hollow organ lumen, comprising:
a wire frame having a flexible tubular shape and a plurality of first and second wire segments each of which extend from a first end of the wire frame to a second end thereof,
at least one of the first wire segments and at least one of the second wire segments each being portions of a respective single length of wire,
the plurality of first and second wire segments having flexible interconnections and defining a plurality of cells, with each of the flexible interconnections being defined by a respective first wire segment and a respective second wire segment being wound about each other at least one complete turn with the flexible interconnections between adjoining cells extending axially along the wire frame, and
each of the first wire segments extending through the flexible interconnections of at least two nonadjoining ones of the cells, and each of the second wire segments extending through the flexible interconnections of at least two nonadjoining ones of the cells, wherein the first wire segments extend in step-wise fashion from the first end of the wire frame to the second end in a counterclockwise direction about the circumference of the tubular shape and the second wire segments extend in step-wise fashion from the first end of the wire frame to the second end in a clockwise direction about the tubular shape.

* * * * *